United States Patent
Mutairi et al.

(10) Patent No.: US 12,352,738 B2
(45) Date of Patent: *Jul. 8, 2025

(54) MIXING MODEL TO DETERMINE THE COMPOSITION OF PRODUCED WATER USING OXYGEN AND HYDROGEN ISOTOPE RATIOS

(71) Applicant: Saudi Arabian Oil Company, Dhahran (SA)

(72) Inventors: Sattam S. Mutairi, Al Khobar (SA); Ahmad A. Mashama, Saihat (SA)

(73) Assignee: Saudi Arabian Oil Company, Dhahran (SA)

(*) Notice: Subject to any disclaimer, the term of this patent is extended or adjusted under 35 U.S.C. 154(b) by 274 days.

This patent is subject to a terminal disclaimer.

(21) Appl. No.: 17/901,510

(22) Filed: Sep. 1, 2022

(65) Prior Publication Data

US 2024/0085394 A1  Mar. 14, 2024

(51) Int. Cl.
  *G01N 33/18* (2006.01)
  *G01N 21/31* (2006.01)
  *H01J 49/26* (2006.01)

(52) U.S. Cl.
  CPC ............. *G01N 33/18* (2013.01); *G01N 21/31* (2013.01); *H01J 49/26* (2013.01)

(58) Field of Classification Search
  CPC ..... G01N 33/2823; G01N 33/18; G01N 21/31
  See application file for complete search history.

(56) References Cited

U.S. PATENT DOCUMENTS

| | | | | |
|---|---|---|---|---|
| 4,743,761 A | * | 5/1988 | Raheim | E21B 43/20 250/259 |
| 5,979,228 A | * | 11/1999 | Smith | G01N 33/246 73/61.41 |
| 8,283,173 B2 | * | 10/2012 | Sukhija | C09K 8/58 436/27 |
| 8,316,934 B2 | * | 11/2012 | Pietrobon | E21B 47/11 166/250.15 |
| 8,666,667 B2 | * | 3/2014 | Michael | E21B 47/10 702/9 |
| 8,823,923 B2 | * | 9/2014 | Berman | G01N 21/3577 356/39 |
| 9,470,665 B2 | * | 10/2016 | Eisenhauer | G01N 30/06 |
| 9,816,972 B2 | * | 11/2017 | Romanak | G01N 33/0004 |

(Continued)

OTHER PUBLICATIONS

U.S. Appl. No. 17/901,473, filed Sep. 1, 2022, Mutairi.

(Continued)

*Primary Examiner* — Tran M. Tran
(74) *Attorney, Agent, or Firm* — Fish & Richardson P.C.

(57) ABSTRACT

The disclosure relates to methods for determining an amount of seawater, an amount of aquifer water, and an amount of original reservoir water in a produced water sample using oxygen and hydrogen isotope ratios. An $^{18}O/^{16}O$ ratio ($\delta^{18}O$) and a D/H ratio ($\delta D$) are measured for a seawater sample, an aquifer water sample, and an original reservoir water sample and are used to make a mixing model. $\delta^{18}O$ and $\delta D$ are measured in a produced water sample and the mixing model can be used to determine the amounts of each constituent in the produced water sample.

20 Claims, 4 Drawing Sheets

(56) References Cited

U.S. PATENT DOCUMENTS

| | | | | |
|---|---|---|---|---|
| 9,829,423 | B2* | 11/2017 | Hinkel | G01N 15/0893 |
| 9,891,331 | B2* | 2/2018 | Hornbostel | G01V 1/38 |
| 10,132,144 | B2* | 11/2018 | Lawson | E21B 43/16 |
| 10,415,379 | B2* | 9/2019 | Lawson | G01N 33/225 |
| 10,494,923 | B2* | 12/2019 | Lawson | G01V 9/007 |
| 10,527,601 | B2* | 1/2020 | Dreyfus | G01V 9/007 |
| 10,533,414 | B2* | 1/2020 | Lawson | G01N 33/2841 |
| 10,559,457 | B2* | 2/2020 | Eiler | H01J 49/0009 |
| 10,808,530 | B1* | 10/2020 | Munk | G01N 33/18 |
| 10,815,777 | B2* | 10/2020 | Collins | G01N 33/2835 |
| 10,995,612 | B2* | 5/2021 | Rouchon | G01N 33/005 |
| 11,041,384 | B2* | 6/2021 | Formolo | E21B 49/00 |
| 11,047,233 | B2* | 6/2021 | Luo | G01N 33/2823 |
| 11,066,929 | B2* | 7/2021 | Lu | E21B 49/02 |
| 11,131,187 | B2* | 9/2021 | Lu | G01K 3/14 |
| 11,237,146 | B2* | 2/2022 | Formolo | E21B 49/00 |
| 11,237,147 | B2* | 2/2022 | Peterson | E21B 47/11 |
| 11,275,024 | B2* | 3/2022 | Yasui | G01N 33/4833 |
| 11,378,714 | B2* | 7/2022 | Eltaher | G01V 5/102 |
| 11,543,398 | B2* | 1/2023 | Kim | G01N 33/182 |
| 11,673,071 | B2* | 6/2023 | Kambouris | A23L 2/38 |
| | | | | 424/613 |
| 11,714,939 | B2* | 8/2023 | Filippov | E21B 47/10 |
| | | | | 703/10 |
| 11,788,999 | B2* | 10/2023 | Wei | G01N 33/005 |
| | | | | 73/40.5 R |
| 11,959,902 | B2* | 4/2024 | Pujol | G01N 33/2823 |
| 2004/0029294 | A1* | 2/2004 | Schmidt | G01N 33/02 |
| | | | | 436/127 |
| 2009/0305322 | A1* | 12/2009 | Hegg | C12Q 1/02 |
| | | | | 435/29 |
| 2016/0178598 | A1* | 6/2016 | Pelletier | G01N 33/2823 |
| | | | | 356/70 |
| 2017/0369495 | A1* | 12/2017 | Jasper | C07D 487/04 |

OTHER PUBLICATIONS

Cantrell et al., "Geology and production significance of dolomite, Arab-D reservoir, Ghawar field, Saudi Arabia," GeoArabia, Jan. 2001, 6(1):45-59, 16 pages.

Carrigan et al., "Geochemical characterization of injected and produced water from Paleozoic oil reservoirs in central Saudi Arabia," International Symposium on Oilfield Chemistry, Feb. 1997, 10 pages.

Horita, "Hydrogen isotope analysis of natural waters using an H2-water equilibration method: a special implication to brines," Chemical Geology, Jan. 1988, 72(1):89-94, 6 pages.

Stenger et al., "Assessing the oil water contact in Haradh Arab-D," 2001 SPE Annual Technical Conference and Exhibition, Sep.-Oct. 2001, 16 pages.

Stenger et al., "Tilted original oil/water contact in the Arab-D reservoir, Ghawar field, Saudi Arabia," GeoArabia, Jan. 2003, 8(1):9-42, 34 pages.

\* cited by examiner

MIXING MODEL TO DETERMINE THE COMPOSITION OF PRODUCED WATER USING OXYGEN AND HYDROGEN ISOTOPE RATIOS

FIELD

The disclosure relates to methods for determining an amount of seawater, an amount of aquifer water, and an amount of original reservoir water in a produced water sample using oxygen and hydrogen isotope ratios. An $^{18}$O/$^{16}$O ratio ($\delta^{18}$O) and a D/H ratio ($\delta$D) are measured for a seawater sample, an aquifer water sample, and an original reservoir water sample and are used to make a mixing model. $\delta^{18}$O and $\delta$D are measured in a produced water sample and the mixing model can be used to determine the amounts of each constituent in the produced water sample.

BACKGROUND

Seawater and/or aquifer water can be used for drilling and enhanced oil recovery operations. Reservoirs can contain seawater from power injectors, aquifer water from gravity injections and residual reservoir connate water. Distinguishing between produced waters and in-situ water formation can be difficult due to the injection of aquifer waters and/or seawater. Often, chemical analyses alone have not been successful in distinguishing water sources.

SUMMARY

The disclosure relates to methods for determining an amount of seawater, an amount of aquifer water, and an amount of original reservoir water in a produced water sample using oxygen and hydrogen isotope ratios. An $^{18}$O/$^{16}$O ratio ($\delta^{18}$O) and a D/H ratio ($\delta$D) are measured for a seawater sample, an aquifer water sample, and an original reservoir water sample and are used to make a mixing model. $\delta^{18}$O and $\delta$D are measured in a produced water sample and the mixing model can be used to determine the amounts of each constituent (seawater, aquifer water and/or original reservoir water) in the produced water sample.

The methods of the disclosure can be used in various beneficial ways, either individually or in combination. As an example, the methods of the disclosure can enable the determination of the source of produced water and the effect of seawater and aquifer water on original in-situ waters. As another example, the methods of the disclosure can be used to make operational decisions enabling time and cost savings during drilling and production operations. As a further example, the methods of the disclosure can be used to identify breakthrough of injection water, monitor water flooding and predict potential scaling problems caused by mixing of incompatible waters. As an additional example, the methods of the disclosure can be used in reservoir health monitoring, water wettability estimations and assessing the success of farcing operations.

Alternatively or additionally, the methods of the disclosure can be used to analyze a mixture of waters with different salinity (e.g. low salinity aquifer water, moderate salinity seawater and/or high salinity reservoir water) which, in general, cannot be distinguished by chemical analysis. In some embodiments, the methods of the disclosure can be compatible with chemical reactions caused by mixing of incompatible waters and chemicals such as scale inhibitors, which may alter the composition of produced water.

Optionally, the methods of the disclosure employ the isotope composition of oxygen ($^{18}$O/$^{16}$O) and hydrogen (D/H) in original reservoir water, aquifer water and injected seawater as each water has distinct geochemistry. Oxygen and hydrogen isotopes can be measured with relatively high accuracy and are generally stable over production timescales.

In a first aspect the disclosure provides a method, including: measuring an $^{18}$O/$^{16}$O ratio ($\delta^{18}$O) and an $^2$H/$^1$H ratio ($\delta$D) for each of a seawater sample, an aquifer water sample, and an original reservoir water sample; measuring $\delta^{18}$O and a $\delta$D in a produced water sample; using the measured $\delta^{18}$O and $\delta$D for the aquifer water sample, the seawater sample and the original reservoir water sample to make a model; and using the model to determine an amount of seawater, an amount of aquifer water, and an amount of original reservoir water in the produced water sample. The produced water sample includes the seawater, the aquifer water, and/or the original reservoir water.

In some embodiments, the model is for a well or formation (t) and is made using:

$$V_A \delta^{18}O\, x_{Seawater}(t) + V_B \delta^{18}O\, y_{Aquifer\ water}(t) + V_C \delta^{18}O\, z_{Reservoir\ water}(t) = V_d\, \delta^{18}O_P(t);$$

and $$V_A \delta D\, x_{Seawater}(t) + V_B \delta D\, y_{Aquifer\ water}(t) + V_C \delta D\, z_{Reservoir\ water}(t) = V_d \delta D_P(t);$$

wherein:
- $\delta^{18}O\, x_{Seawater}$, $\delta^{18}O\, y_{Aquifer\ water}$, and $\delta^{18}O\, z_{Reservoir\ water}$ are the oxygen isotope ratios in in the seawater, aquifer water and original reservoir water, respectively;
- $\delta D\, x_{Seawater}$, $\delta D\, y_{Aquifer\ water}$, and $\delta D\, z_{Reservoir\ water}$ are the hydrogen isotope ratios in in the seawater, aquifer water and original reservoir water, respectively;
- $V_A$, $V_B$ and $V_C$ are relative volume fractions of the seawater, aquifer water and original reservoir water respectively;
- $V_D$ is a mixing proportion used in the model; and
- $\delta^{18}O_P$ and $\delta D_P$ are the oxygen and hydrogen isotope ratios, respectively, in the produced water sample.

In some embodiments: the model includes first, second and third endpoints; $V_A$, $V_B$ and $V_C$ correspond to relative volume percentages of the seawater sample, the aquifer water sample, and the original reservoir water sample, respectively; the first endpoint corresponds to $V_A=1$, $V_B=0$ and $V_C=0$; the second endpoint corresponds to $V_A=0$, $V_B=1$ and $V_C=0$; and the third endpoint corresponds to $V_A=0$, $V_B=0$ and $V_C=1$.

In some embodiments: the model includes first, second and third outer lines that connect the endpoints to define a triangle; the first outer line corresponds to $V_A$ being equal to zero while varying $V_B$ and $V_C$; the second outer line corresponds to $V_B$ being equal to zero while varying $V_A$ and $V_C$; and the third outer line corresponds to $V_C$ being equal to zero while varying $V_A$ and $V_B$.

In some embodiments: the model includes grid lines that connect the outer lines; and each grid line corresponds to one member selected from the group consisting of $V_A$, $V_B$ and $V_C$ being at a constant value between 0 and 1 and varying the other two members selected from the group consisting of $V_A$, $V_B$ and $V_C$.

In some embodiments: each endpoint corresponds to a mixture including only one member selected from the group consisting of the seawater sample, the aquifer water sample, and the original reservoir water sample; each outer line corresponds to a mixture including two members selected from the group consisting of the seawater sample, the aquifer water sample, and the original reservoir water sample; and each grid line corresponds to a mixture including the seawater sample, the aquifer water sample, and the original reservoir water sample.

In some embodiments: a produced water sample including only one member selected from the group consisting of the seawater sample, the aquifer water sample, and the original reservoir water sample plots close to its corresponding endpoint; a produced water sample including only two members selected from the group consisting of the seawater sample, the aquifer water sample, and the original reservoir water sample plots along the outer lines at a position corresponding to an amount of each of the two members; and a produced water sample including the seawater sample, the aquifer water sample, and the original reservoir water sample plots in at a position within the triangle corresponding to an amount of each of the seawater sample, the aquifer water sample, and the original reservoir water sample.

In some embodiments: the model includes endpoints that correspond to mixtures including only one member selected from the group consisting of the seawater sample, the aquifer water sample, and the original reservoir water sample; the model includes outer lines connecting the endpoints that correspond to mixtures including only two members selected from the group consisting of the seawater sample, the aquifer water sample, and the original reservoir water sample; the outer lines define a triangle; and the model includes grid lines that connect the outer lines that correspond to mixtures including the seawater sample, the aquifer water sample, and the original reservoir water sample.

In some embodiments: a produced water sample including only one member selected from the group consisting of the seawater sample, the aquifer water sample, and the original reservoir water sample plots close to the corresponding endpoint; a produced water sample including two members selected from the group consisting of the seawater sample, the aquifer water sample, and the original reservoir water sample plots along the outer lines at a position corresponding to an amount of each of the two members; and a produced water sample including the seawater sample, the aquifer water sample, and the original reservoir water sample plots at a position within the triangle corresponding to an amount of each of the seawater sample, the aquifer water sample, and the original reservoir water sample.

In some embodiments, the seawater has a $\delta D$ of $-5$ to 30.

In some embodiments, the seawater has a $\delta^{18}O$ of $-5$ to 7.

In some embodiments, the aquifer water has $\delta D$ of $-50$ to $-5$.

In some embodiments, the aquifer water has a $\delta^{18}O$ of $-10$ to 3.

In some embodiments, the original reservoir water has a $\delta D$ of $-40$ to 8.

In some embodiments, the original reservoir water has a $\delta^{18}O$ of $-2$ to 8.

In some embodiments, the produced water is from a production well in fluid communication with an underground reservoir.

In some embodiments, the produced water is from a flowback operation.

In some embodiments, the seawater is injected into the underground reservoir.

In some embodiments, the aquifer water is injected into the underground reservoir.

In some embodiments, an amount of $^{16}O$, an amount of $^{18}O$, an amount of $^{1}H$ and/or an amount of $^{2}H$ is measured using at least one of mass spectrometry and wavelength-scanned cavity ring-down spectroscopy.

DETAILED DESCRIPTION

Figure 1:
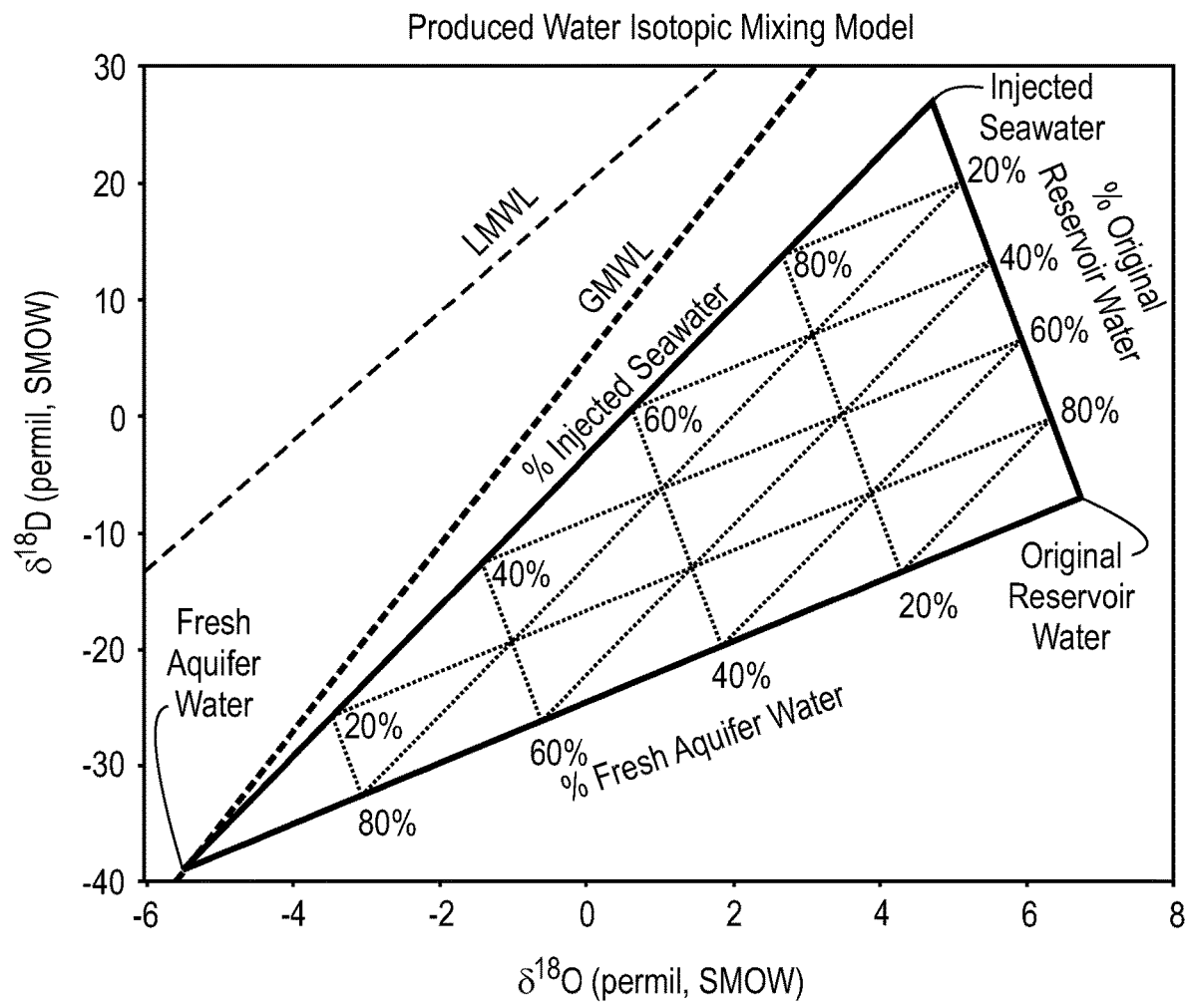
FIG. 1 is a plot of $\delta D$ versus $\delta^{18}O$ according to a mixing model.

Oxygen and hydrogen isotope ratios can be reported relative to Vienna Standard Mean Ocean Water (VSMOW) using the delta notation:

$$\delta^{18}O(\text{\textperthousand}) = 1000\left[\frac{\left(\frac{18_O}{16_O}\right)_{SAMPLE}}{\left(\frac{18_O}{16_O}\right)_{VSMOW}} - 1\right] \quad (1)$$

$$\delta D(\text{\textperthousand}) = 1000\left[\frac{\left(\frac{D}{H}\right)_{SAMPLE}}{\left(\frac{D}{H}\right)_{VSMOW}} - 1\right] \quad (2)$$

where $^{18}O/^{16}O$ and D/H ($^{2}H/^{1}H$) are atomic abundance ratios.

Mixing proportions of oxygen and hydrogen isotopes for a well or formation (t) with three mixing components and relative volume fractions $V_A$, $V_B$ and $V_C$ yield the equations:

$$V_A \delta^{18}O_{Seawater} \, x_{Seawater}(t) + \\ V_B \delta^{18}O_{Aquifer\ water} \, y_{Aquifer\ water}(t) + \\ V_C \delta^{18}O_{Reservoir\ water} \, z_{Reservoir\ water}(t) = \\ V_D \delta^{18}O_P(t) \quad (1)$$

and $$V_A \delta D \, x_{Seawater}(t) + V_B \delta D \, y_{Aquifer\ water}(t) + \\ V_C \delta D \, z_{Reservoir\ water}(t) = V_D \delta D_P(t) \quad (2)$$

wherein: $\delta^{18}O\ x_{Seawater}$, $\delta^{18}O\ y_{Aquifer\ water}$, and $\delta^{18}O\ z_{Reservoir\ water}$ are the oxygen isotope ratios in in the seawater, aquifer water and original reservoir water, respectively; $\delta D\ x_{Seawater}$, $\delta D\ y_{Aquifer\ water}$, and $\delta D\ z_{Reservoir\ water}$ are the hydrogen isotope ratios in in the seawater, aquifer water and original reservoir water, respectively; $V_A$, $V_B$ and $V_C$ are the relative volume fractions of the seawater, aquifer water and original reservoir water respectively; $V_D$ is the mixing proportion used in the model; and $\delta^{18}O_P$ and $\delta D_P$ are the oxygen and hydrogen isotope ratios in the produced water sample. Typically, the value of $V_D$ is 1.

In the methods of the disclosure, the oxygen and hydrogen isotope ratios for seawater, aquifer water and original reservoir water are available, e.g., measured or otherwise determined or provided. Once obtained, the values can be used to construct the model. Such a model is depicted in FIGS. 1-4. These figures are explained in more detail below.

Generally, the model contains three endpoints, where each endpoint corresponds to one of the three components (the seawater, the aquifer water and the original reservoir water). In FIGS. 1-4, the endpoints correspond to the vertices of the triangle. Each endpoint can be determined by setting one of the volume fractions $V_A$, $V_B$ and $V_C$, corresponding to the fraction of seawater, aquifer water and original reservoir water respectively, to 1, while setting the other two volume fractions to 0. Specifically, using $V_A=1$, $V_B=0$ and $V_C=0$; $V_A=0$; $V_B=1$ and $V_C=0$; and $V_A=0$, $V_B=0$ and $V_C=1$ in Equations 3 and 4 provides the three endpoints.

The model additionally contains outer lines connecting the endpoints that correspond to mixtures of two of the components. The outer lines can be obtained by setting one of $V_A$, $V_B$ and $V_C$ to 0 and varying the other two parameters. The model can further contain grid lines that connect the outer lines that correspond to mixtures of the three components. The grid lines can be obtained by holding one of $V_A$, $V_B$ and $V_C$ at a constant value between 0 and 1 and varying the other two components.

Generally, a produced water sample containing only one of the components will plot close to the corresponding endpoint. A produced water sample containing only two of the components will plot along the outer lines at a position corresponding to an amount of each of the two components. A produced water sample containing all three of the components will plot in the center of the triangle at a position corresponding to an amount of each of the three components.

Generally, isotope concentrations in a water sample can be measured using any appropriate technique. As an example, in certain embodiments, the amount of $^{16}O$, $^{18}O$ D ($^2H$) and/or H ($^1H$) is measured using a wavelength-scanned cavity ring-down spectroscopy (WS-CRDS). As another example, in certain embodiments, the amount of $^{16}O$, $^{18}O$, D and/or H can be measured using mass spectrometry.

In certain embodiments, the $\delta^{18}O$ of the seawater, the aquifer water and/or the original reservoir water depends on the geographical location of the water. In certain embodiments, the seawater has a $\delta^{18}O$ of at least −5 (e.g., at least −4, at least −3, at least −2, at least −1, at least 0, at least 1, at least 2, at least 3, at least 4, at least 5) and at most 7 (e.g., at most 6, at most 5, at most 4, at most 3, at most 2, at most 1, at most 0, at most −1, at most −2, at most −3). In certain embodiments, the aquifer water has a $\delta^{18}O$ of at least −10 (e.g., at least −9, at least −8, at least −7, at least −6, at least −5) and at most −3 (e.g., at most −4, at most −5, at most −6, at most −7, at most −8). In certain embodiments, the original reservoir water has a $\delta^{18}O$ of at least −2 (e.g., at least −1, at least 0, at least 1, at least 2, at least 3, at least 4, at least 5, at least 6) and at most 8 (e.g., at most 7, at most 6, at most 5, at most 4, at most 3, at most 2, at most 1, at most 0).

In some embodiments, the $\delta D$ of the seawater, the aquifer water and/or the original reservoir water depends on the geographical location of the water. In some embodiments, the seawater has a $\delta D$ of at least −5 (e.g., at least −4, at least −3, at least −2, at least −1, at least 0, at least 5, at least 10, at least 15, at least 25) and at most 30 (e.g., at most 29, at most 28, at most 27, at most 26, at most 25, at most 20, at most 15, at most 10, at most 5, at most 0). In some embodiments, the aquifer water has a $\delta D$ of at least −50 (e.g., at least −49, at least −48, at least −47, at least −46, at least −45, at least −40, at least −35, at least −30, at least −25, at least −20, at least −15, at least −10) and at most −5 (e.g., at most −6, at most −7, at most −8, at most −9, at most −10, at most −15, at most −20, at most −25, at most −30, at most −35, at most −40, at most −45). In some embodiments, the original reservoir water has a $\delta D$ of at least −40 (e.g., at least −39, at least −38, at least −37, at least −36, at least −35, at least −30, at least −25, at least −20, at least −15, at least −10, at least −5, at least 0, at least 5) and at most 8 (e.g., at most 7, at most 6, at most 5, at most 0, at most −5, at most −10, at most −15, at most −20, at most −25, at most −30, at most −35).

EXAMPLES

Example 1—Construction of Mixing Model $\delta^{18}O$ and $\delta D$ were measured for samples of seawater, aquifer water and original reservoir water. $\delta^{18}O$ and $\delta D$ were measured using both wavelength-scanned cavity ring-down spectroscopy mass spectrometry.

$\delta^{18}O$ and $\delta D$ were measured using a Picarro L2130-i Laser Cavity Ring-Down Spectroscopy (CRDS) instrument. 5 μl of sample was injected into a vaporizer a total of 8 times. The temperature and pressure were kept constant at 110° C. and 3.5 psig inside the line to ensure total and instantaneous vaporization of the water without isotopic fractionation.

For mass spectrometry measurements, 5 ml aliquots of sample were placed in 25 ml glass vials, attached to a vacuum manifold and immersed in a water bath regulated to 18.0±0.2° C. The manifold was used to remove air and add 0.7-0.9 bars of hydrogen gas (for hydrogen isotope measurements) or carbon dioxide (for oxygen isotope measurements). Isotopic equilibration between hydrogen gas and water was achieved after 60-90 minutes with the aid of 2 mg of Pt catalyst (as described in Horita, 1988). Isotopic equilibration between carbon dioxide and water was achieved overnight without the use of a catalyst. The equilibrated gases were passed over acetone slush (−90--96° C.) to remove water vapor. The gases were then introduced into a dual-inlet Finnigan-MAT Delta S stable isotope ratio mass spectrometer using automated valves. Water standards (USGS-48, USGS-47, USGS-48, USGS-50, PRIMARY VSMOW STANDARD, and three other lab made standards) were used to calibrate the isotope ratios and report them relative to standard mean ocean water (SMOW) using delta notation. Reproducibilities, estimated by pooling standard deviations for replicate analyses of standards were ±0.13‰ for $\delta^{18}O$ and ±1.6‰ for $\delta D$.

The oxygen and hydrogen isotope ratios for the seawater, aquifer and original reservoir water samples measured are presented in table 1.

TABLE 1

Oxygen and hydrogen isotope ratios for source water samples

| Component | $\delta^{18}O$ | $\delta D$ |
|---|---|---|
| Seawater | 4.7 | 27 |
| Aquifer water | −5.5 | −39 |
| Original reservoir water | 6.7 | −18.4 |

The values of $V_A$, $V_B$ and $V_C$ were each set to 1 while the other two were set to 0 in equations 2 and 3 to provide the values for the endpoints of the model, as shown in table 2.

TABLE 2

Oxygen and hydrogen isotope ratios model endpoints

| Fraction of seawater ($V_A$) | Fraction of aquifer water ($V_B$) | Fraction of original reservoir water ($V_C$) | $\delta^{18}O$ | $\delta D$ |
|---|---|---|---|---|
| 1 | 0 | 0 | 4.7 | 27 |
| 0 | 1 | 0 | −5.5 | −39 |
| 0 | 0 | 1 | 6.7 | −18.4 |

The outer lines and grid lines of the model were calculated by varying the values of $V_A$, $V_B$ and $V_C$ in equations 3 and 4. Table 3 shows the values of $\delta^{18}O$ and $\delta D$ used to make the outer lines and the grid lines.

TABLE 3

Oxygen and hydrogen isotope ratios model outer lines and grid lines

| Fraction of seawater ($V_A$) | Fraction of aquifer water ($V_B$) | Fraction of original reservoir water ($V_C$) | $\delta^{18}O$ | $\delta D$ |
|---|---|---|---|---|
| 0.2 | 0.8 | 0 | −3.46 | −25.8 |
| 0.2 | 0 | 0.8 | 6.30 | −0.2 |
| 0.4 | 0.6 | 0 | −1.42 | −12.6 |
| 0.4 | 0 | 0.6 | 5.90 | 6.6 |
| 0.6 | 0.4 | 0 | 0.62 | 0.6 |
| 0.6 | 0 | 0.4 | 5.50 | 13.4 |
| 0.8 | 0.2 | 0 | 2.66 | 13.8 |
| 0.8 | 0 | 0.2 | 5.10 | 20.2 |
| 0 | 0.2 | 0.8 | 4.26 | −13.4 |
| 0.8 | 0.2 | 0 | 2.66 | 13.8 |
| 0 | 0.4 | 0.6 | 1.82 | −19.8 |
| 0.6 | 0.4 | 0 | 0.62 | 0.6 |
| 0 | 0.6 | 0.4 | −0.62 | −26.2 |
| 0.4 | 0.6 | 0 | −1.42 | −12.6 |
| 0 | 0.8 | 0.2 | −3.06 | −32.6 |
| 0.2 | 0.8 | 0 | −3.46 | −25.8 |
| 0 | 0.8 | 0.2 | −3.06 | −32.6 |
| 0.8 | 0 | 0.2 | 5.1 | 20.2 |
| 0 | 0.6 | 0.4 | −0.62 | −26.2 |
| 0.6 | 0 | 0.4 | 5.5 | 13.4 |
| 0 | 0.4 | 0.6 | 1.82 | −19.8 |
| 0.4 | 0 | 0.6 | 5.9 | 6.6 |
| 0 | 0.2 | 0.8 | 4.26 | −13.4 |
| 0.2 | 0 | 0.8 | 6.3 | −0.2 |

Figure 2:
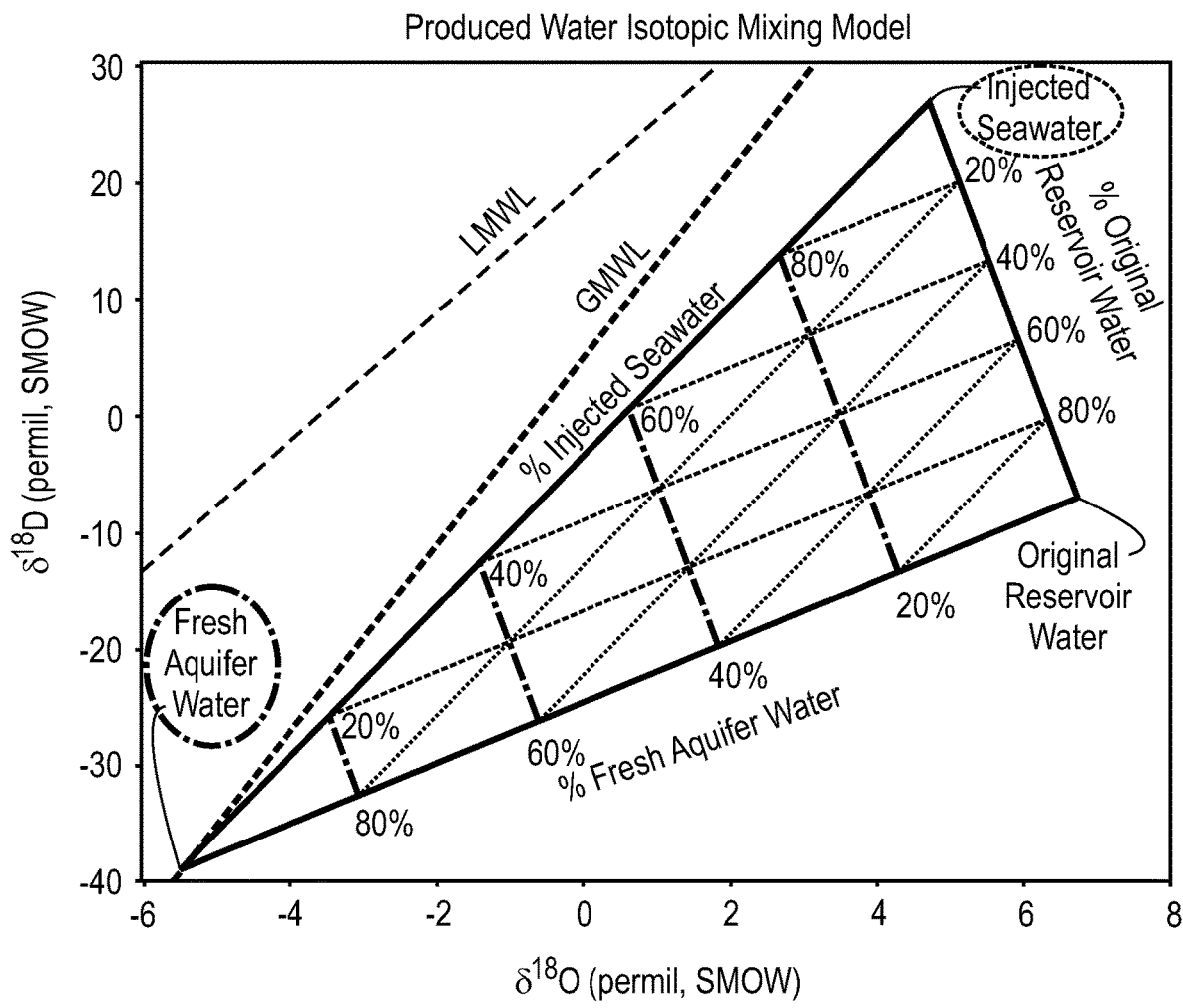
FIG. 2 is a plot of $\delta D$ versus $\delta^{18}O$ according to a mixing model.

The mixing model is shown in FIG. 1. FIG. 2 shows the mixing model where the grid lines for the aquifer water and injected seawater are dotted and dashed lines and dashed lines, respectively. The global meteoric water line (GMW) and local meteoric water lime (LMWL) are also plotted in FIGS. 1 and 2.

Example 2—Characterization of Produced Water Samples

The mixing model generated in Example 1 was used to determine the composition of produced water samples. $\delta^{18}O$ and $\delta D$ of 128 produced water samples from five different wells in the same field and reservoir taken during different field operations were determined using the methods described in Example 1.

Figure 3:
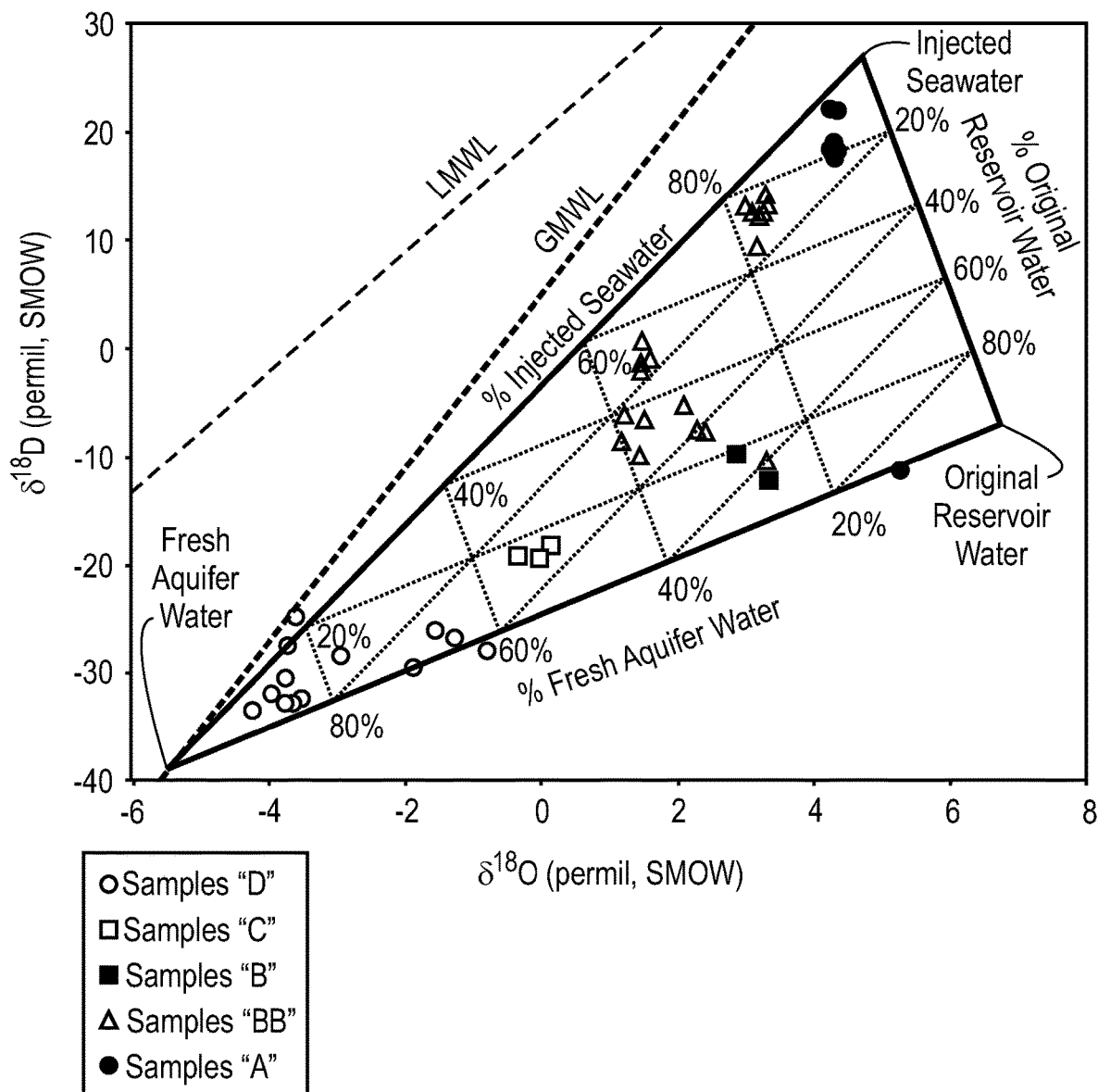
FIG. 3 is a plot of $\delta D$ versus $\delta^{18}O$ according to a mixing model with produced water samples plotted on the mixing model.

FIG. 3 shows the produced water samples plotted on the mixing model. The global meteoric water line (GMW) and local meteoric water lime (LMWL) are also plotted in FIG. 3.

Produced water samples "A" plot very closed to the injected seawater source end-member, suggesting that the produced waters was composed almost entirely of injected seawater (90% injected seawater water).

Produced water samples "B" were composed of nearly 60% original reservoir water, less than 20% of injected seawater and slightly more than 20% fresh aquifer water source.

Produced water samples "BB" were divided into two clusters. Some samples contained more than 70% injected seawater. The other set of samples plotted in the middle of the model, indicating that they were distributed between the three sources. This suggests that the well had periods of seawater and fresh water injection into the reservoir causing samples to possess mixtures of all sources of water.

Produced water samples "C" also had mixtures of the water sources. The samples had about 50% fresh aquifer water source, less than 20% injected seawater source and 30% original reservoir water source. This suggests that the produced water samples were mostly aquifer water used during drilling operation. It also indicates that during the flowback operation, small quantities of original reservoir water flowed and mixed with the aquifer water.

Figure 4:
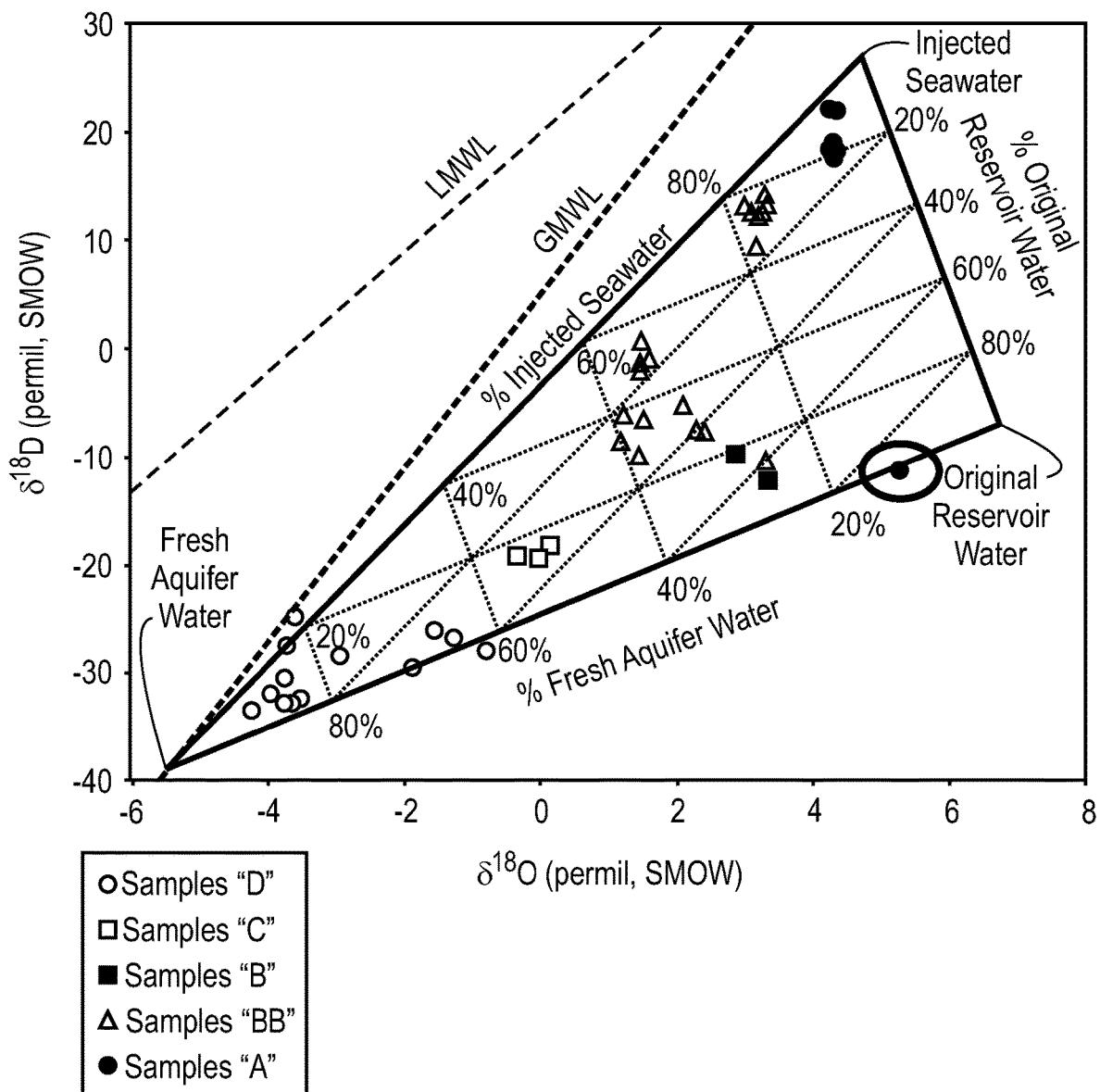
FIG. 4 is a plot of $\delta D$ versus $\delta^{18}O$ according to a mixing model with produced water samples plotted on the mixing model.

Produced water samples "D" plotted near the aquifer water endpoint and along the outer line between aquifer water and original reservoir water, suggesting a mix of 20% original reservoir water and 80% injected seawater. FIG. 4 shows FIG. 3 with one sample from "D" circled. This data point was identified using the model as about 90% original reservoir water and about 10% fresh aquifer water.

The mixing model was successfully applied to produced water to help predict and estimate the source of produced water and the effect of seawater and/or aquifer water on the original reservoir water. This information can help make quick field operation decisions, thereby saving time and reducing costs in drilling and production operations.

What is claimed:

1. A method, comprising:
   measuring an $^{18}O/^{16}O$ ratio ($\delta^{18}O$) and an $^{2}H/^{1}H$ ratio ($\delta D$) for each of a seawater sample, an aquifer water sample, and an original reservoir water sample;
   measuring a $\delta^{18}O$ and a $\delta D$ in a produced water sample;
   using the measured $\delta^{18}O$ and $\delta D$ for the aquifer water sample, the seawater sample and the original reservoir water sample to make a model; and
   using the model to determine an amount of seawater, an amount of aquifer water, and an amount of original reservoir water in the produced water sample,
   wherein the produced water sample comprises at least one member selected from the group consisting of the seawater, the aquifer water, and the original reservoir water.

2. The method of claim 1, wherein the model is for a well or formation (t) and is made using:

$$V_A \delta^{18}O\, x_{Seawater}(t) + V_B \delta^{18}O\, y_{Aquifer\,water}(t) + V_C \delta^{18}O\, z_{Reservoir\,water}(t) = V_D \delta^{18}O_P(t);$$

and $$V_A \delta D\, x_{Seawater}(t) + V_B \delta D\, y_{Aquifer\,water}(t) + V_C \delta D\, z_{Reservoir\,water}(t) = V_D \delta D_P(t);$$

wherein:
   $\delta^{18}O\, x_{Seawater}$, $\delta_{18}O\, y_{Aquifer\,water}$, and $\delta^{18}O\, z_{Reservoir\,water}$ are the measured oxygen isotope ratios in the seawater, aquifer water and original reservoir water, respectively;
   $\delta D\, x_{Seawater}$, $\delta D\, y_{Aquifer\,water}$, and $\delta D\, z_{Reservoir\,water}$ are the measured hydrogen isotope ratios in the seawater, aquifer water and original reservoir water, respectively;
   $V_A$, $V_B$ and $V_C$ are relative volume fractions of the seawater, aquifer water and original reservoir water respectively;
   $V_D$ is a mixing proportion used in the model; and
   $\delta^{18}O_P$ and $\delta D_P$ are the oxygen and hydrogen isotope ratios, respectively, in the produced water sample.

3. The method of claim 2, wherein:
   the model comprises first, second and third endpoints;
   $V_A$, $V_B$ and $V_C$ correspond to relative volume percentages of the seawater sample, the aquifer water sample, and the original reservoir water sample, respectively the first endpoint corresponds to $V_A=1$, $V_B=0$ and $V_C=0$;
the second endpoint corresponds to $V_A=0$; $V_B=1$ and $V_C=0$; and
the third endpoint corresponds to $V_A=0$, $V_B=0$ and $V_C=1$.

4. The method of claim 3, wherein:
the model comprises first, second and third outer lines that connect the endpoints to define a triangle;
the first outer line corresponds to $V_A$ being equal to zero while varying $V_B$ and $V_C$;
the second outer line corresponds to $V_B$ being equal to zero while varying $V_A$ and $V_C$; and
the third outer line corresponds to $V_C$ being equal to zero while varying $V_A$ and $V_B$.

5. The method of claim 4, wherein:
the model comprises grid lines that connect the outer lines; and
each grid line corresponds to one member selected from the group consisting of $V_A$, $V_B$ and $V_C$ being at a constant value between 0 and 1 and varying the other two members selected from the group consisting of $V_A$, $V_B$ and $V_C$.

6. The method of claim 5, wherein:
each endpoint corresponds to a mixture comprising only one member selected from the group consisting of the seawater sample, the aquifer water sample, and the original reservoir water sample;
each outer line corresponds to a mixture comprising two members selected from the group consisting of the seawater sample, the aquifer water sample, and the original reservoir water sample; and
each grid line corresponds to a mixture comprising the seawater sample, the aquifer water sample, and the original reservoir water sample.

7. The method of claim 6, wherein:
a produced water sample comprising only one member selected from the group consisting of the seawater sample, the aquifer water sample, and the original reservoir water sample plots close to its corresponding endpoint;
a produced water sample comprising only two members selected from the group consisting of the seawater sample, the aquifer water sample, and the original reservoir water sample plots along the outer lines at a position corresponding to an amount of each of the two members; and
a produced water sample comprising the seawater sample, the aquifer water sample, and the original reservoir water sample plots in at a position within the triangle corresponding to an amount of each of the seawater sample, the aquifer water sample, and the original reservoir water sample.

8. The method of claim 1, wherein:
the model comprises endpoints that correspond to mixtures comprising only one member selected from the group consisting of the seawater sample, the aquifer water sample, and the original reservoir water sample;
the model comprises outer lines connecting the endpoints that correspond to mixtures comprising only two members selected from the group consisting of the seawater sample, the aquifer water sample, and the original reservoir water sample;
the outer lines define a triangle; and
the model comprises grid lines that connect the outer lines that correspond to mixtures comprising the seawater sample, the aquifer water sample, and the original reservoir water sample.

9. The method of claim 8, wherein:
when the produced water sample comprises only one member selected from the group consisting of the seawater sample, the aquifer water sample, and the original reservoir water sample, the produced water sample plots close to the corresponding endpoint;
when the produced water sample comprises two members selected from the group consisting of the seawater sample, the aquifer water sample, and the original reservoir water sample, the produced water sample plots along the outer lines at a position corresponding to an amount of each of the two members; and
when the produced water sample comprises the seawater sample, the aquifer water sample, and the original reservoir water sample, the produced water sample plots at a position within the triangle corresponding to an amount of each of the seawater sample, the aquifer water sample, and the original reservoir water sample.

10. The method of claim 1, wherein the seawater has a $\delta D$ of −5 to 30.

11. The method of claim 1, wherein the seawater has a $\delta^{18}O$ of −5 and to 7.

12. The method of claim 1, wherein the aquifer water has $\delta D$ of −50 to −5.

13. The method of claim 1, wherein the aquifer water has a $\delta^{18}O$ of −10 to 3.

14. The method of claim 1, wherein the original reservoir water has a $\delta D$ of −40 to 8.

15. The method of claim 1, wherein the original reservoir water has a $\delta^{18}O$ of −2 to 8.

16. The method of claim 1, wherein the produced water is from a production well in fluid communication with an underground reservoir.

17. The method of claim 16, wherein the produced water is from a flowback operation.

18. The method of claim 16, wherein at least one of the following holds:
the seawater is injected into the underground reservoir; or
the aquifer water is injected into the underground reservoir.

19. The method of claim 1, wherein at least one member selected from the group consisting of an amount of $^{16}O$, an amount of $^{18}O$, an amount of $^1H$ and an amount of $^2H$ is measured using at least one of mass spectrometry and wavelength-scanned cavity ring-down spectroscopy.

20. The method of claim 1, further comprising:
using the determined amount of seawater, amount of aquifer water, and amount of original reservoir water in the produced water sample to:
perform or modify a drilling operation in an underground reservoir from which the produced water sample was produced; or
perform or modify a production operation in the underground reservoir from which the produced water sample was produced.

* * * * *